(12) United States Patent
Kim et al.

(10) Patent No.: US 11,427,522 B2
(45) Date of Patent: Aug. 30, 2022

(54) ISOPROPYL ALCOHOL PURIFICATION METHOD

(71) Applicant: LG CHEM, LTD., Seoul (KR)

(72) Inventors: Sung Kyun Kim, Daejeon (KR); Sung Kyu Lee, Daejeon (KR); Saeun Park, Daejeon (KR)

(73) Assignee: LG CHEM, LTD., Seoul (KR)

( * ) Notice: Subject to any disclaimer, the term of this patent is extended or adjusted under 35 U.S.C. 154(b) by 54 days.

(21) Appl. No.: 16/961,570

(22) PCT Filed: Jul. 26, 2019

(86) PCT No.: PCT/KR2019/009326
§ 371 (c)(1),
(2) Date: Jul. 10, 2020

(87) PCT Pub. No.: WO2020/111439
PCT Pub. Date: Jun. 4, 2020

(65) Prior Publication Data
US 2021/0061741 A1    Mar. 4, 2021

(30) Foreign Application Priority Data
Nov. 30, 2018   (KR) .................. 10-2018-0152173

(51) Int. Cl.
*C07C 29/82*   (2006.01)
*C07C 31/10*   (2006.01)
(52) U.S. Cl.
CPC ............. *C07C 29/82* (2013.01); *C07C 31/10* (2013.01)

(58) Field of Classification Search
CPC ................................ C07C 29/82; C07C 31/10
See application file for complete search history.

(56) References Cited

U.S. PATENT DOCUMENTS 5,868,906 A * 2/1999 Adams .................. C07C 29/80
203/18
6,733,637 B1   5/2004 Burton et al.
(Continued)

FOREIGN PATENT DOCUMENTS

CN   105712839 A  *  6/2016
CN   105712839 A     6/2016
(Continued)

OTHER PUBLICATIONS

CN105712839A_English Translation (Year: 2016).*
(Continued)

*Primary Examiner* — Youngsul Jeong
(74) *Attorney, Agent, or Firm* — Dentons US LLP

(57) ABSTRACT

The purification method of isopropyl alcohol including: feeding a feed including isopropyl alcohol, water, and a byproduct comprising normal propyl alcohol to an azeotropic distillation purification tower; separating an azeotrope comprising isopropyl alcohol, normal-propyl alcohol, and water from the top of the azeotropic distillation purification tower and feeding the azeotrope to a dehydration tower; separating the isopropyl alcohol and the normal-propyl alcohol from the bottom of the dehydration tower and feeding the isopropyl alcohol and the normal-propyl alcohol to a normal-propyl alcohol purification tower; and separating the isopropyl alcohol from the top of the normal propyl alcohol purification tower.

8 Claims, 1 Drawing Sheet

(56) References Cited

U.S. PATENT DOCUMENTS

| | | |
|---|---|---|
| 7,235,702 B2 | 6/2007 | Chuang et al. |
| 2015/0083578 A1 | 3/2015 | Lee et al. |
| 2016/0200649 A1 | 7/2016 | Park et al. |
| 2016/0207858 A1 | 7/2016 | Park et al. |

FOREIGN PATENT DOCUMENTS

| | | |
|---|---|---|
| KR | 10-1999-0014837 A | 2/1999 |
| KR | 10-2004-0085710 A | 10/2004 |
| KR | 10-0790413 B1 | 1/2008 |
| KR | 10-2014-0032331 A | 3/2014 |
| KR | 10-2015-0021485 A | 3/2015 |
| KR | 10-1662895 B1 | 10/2016 |

OTHER PUBLICATIONS

Chang et al. (Design and control of a complete azeotropic distillation system incorporating stripping columns for isopropyl alcohol dehydration, 2012, I&EC Research, vol. 21. pp. 2997-3006) (Year: 2012).*

Chang, et al., Design and Control of a Complete Azeotropic Distillation System Incorporating Stripping Columns for Isopropyl Alcohol Dehydration, Ind. Eng.Chem. Res., vol. 51, pp. 2997-3006 (2012).

\* cited by examiner

FIG. 1 – RELATED ART
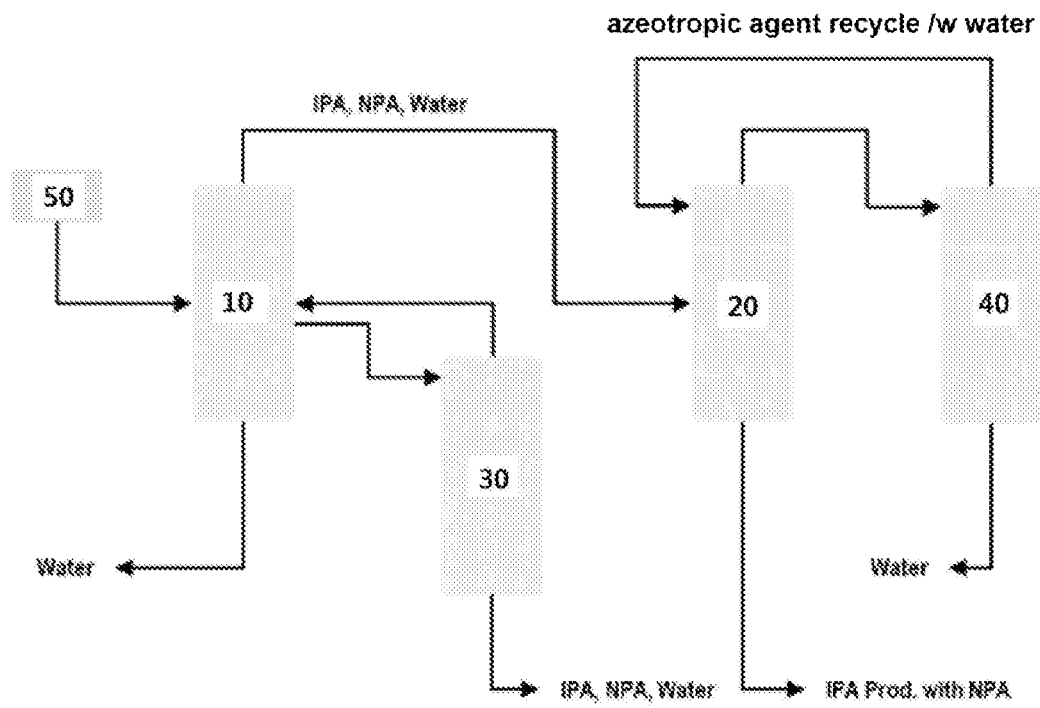
FIG. 2
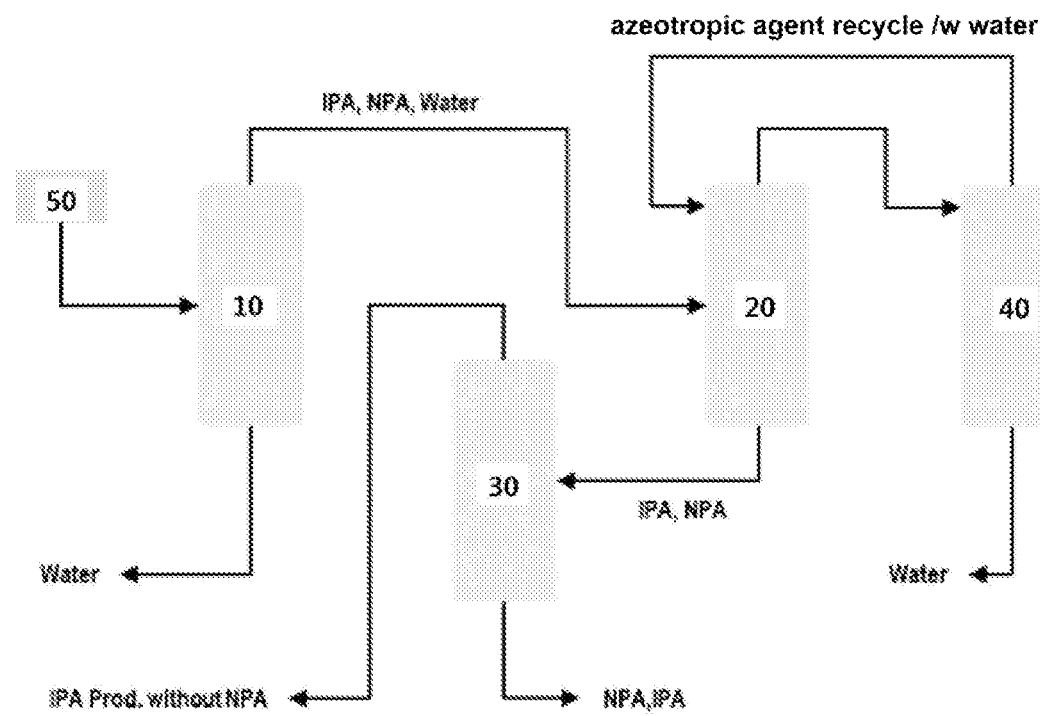

ISOPROPYL ALCOHOL PURIFICATION METHOD

CROSS-REFERENCE TO RELATED APPLICATIONS

This application is a U.S. national stage of international Application No. PCT/KR2019/009326 filed Jul. 26, 2019, and claims priority to and the benefit of Korean Patent Application No. 10-2018-0152173 filed in the Korean Intellectual Property Office on Nov. 30, 2018, the entire contents of which are incorporated herein by reference.

TECHNICAL FIELD

The present application relates to a purification method of isopropyl alcohol.

BACKGROUND

Isopropyl alcohol (IPA) has various uses including as a cleaning agent in the electronic industry such as the manufacture of, for example, semiconductors and liquid crystal display (LCD).

IPA may be prepared using, for example, propylene, acetone, or the like as a raw material. In most cases, an IPA reactant comprising a large amount of water is obtained during the process of preparing IPA, and the reactant forms an azeotrope comprising water. That is, water having a boiling point of about 100° C. and IPA having a boiling point of about 82.5° C. at normal pressure form an azeotrope with 87.9 wt % of IPA at an azeotropic temperature of about 80.4° C., and accordingly, it is required to efficiently prepare high-purity IPA by removing water from the feed, and which consumes a significant amount of energy in a simple distillation process. As a method for obtaining high-purity IPA from the azeotrope, extraction, a distillation method of adding an azeotropic agent which is a material that forms an azeotropic product, or the like is known.

SUMMARY

The present application provides a purification method of isopropyl alcohol.

An exemplary embodiment of the present application provides a method for purifying isopropyl alcohol, the method comprising:

feeding a feed comprising: isopropyl alcohol; water; and a byproduct comprising normal-propyl alcohol to an azeotropic distillation purification tower;

separating an azeotrope comprising isopropyl alcohol, normal-propyl alcohol, and water from the top of the azeotropic distillation purification tower and feeding the azeotrope to a dehydration tower;

separating the isopropyl alcohol and the normal-propyl alcohol from the bottom of the dehydration tower and feeding the isopropyl alcohol and the normal-propyl alcohol to a normal-propyl alcohol purification tower; and separating the isopropyl alcohol from the top of the normal-propyl alcohol purification tower.

The purification method of isopropyl alcohol according to an exemplary embodiment of the present application may increase the separation efficiency of isopropyl alcohol (IPA) and normal-propyl alcohol (NPA) because water is removed by feeding an azeotrope comprising isopropyl alcohol, normal-propyl alcohol, and water to a dehydration tower, and then separating the isopropyl alcohol and the normal-propyl alcohol.

Further, since the purification method of isopropyl alcohol according to an exemplary embodiment of the present application may minimize the content of normal-propyl alcohol in a final product, ultrapure (99.8 wt % or more) isopropyl alcohol may be prepared.

BRIEF DESCRIPTION OF DRAWINGS

FIG. 1 is a process diagram schematically illustrating a purification method of isopropyl alcohol according to the related art.

FIG. 2 is a process diagram schematically illustrating a purification method of isopropyl alcohol according to an exemplary embodiment of the present application.

REFERENCE NUMERALS AND SYMBOLS USED HEREIN

10: Azeotropic distillation purification tower
20: Dehydration tower
30: Normal-propyl alcohol purification tower
40: Water recovery tower
50: Feed

DETAILED DESCRIPTION

Hereinafter, the present application will be described in more detail. A process diagram of a purification method of isopropyl alcohol according to the related art is schematically illustrated in FIG. 1.

As illustrated in FIG. 1, in the related art, water was removed into the bottom of an azeotropic distillation purification tower 10, an azeotrope comprising isopropyl alcohol, normal-propyl alcohol, and water was separated from the top of the azeotropic distillation purification tower 10, and normal-propyl alcohol comprising isopropyl alcohol and water was removed from a normal-propyl alcohol purification tower 30 connected to a side stripping structure. That is, the normal-propyl alcohol purification tower 30 in the related art has a structure in which water is inevitably present. However, at atmospheric pressure, the azeotropic point of isopropyl alcohol and water is 80.4° C. and the azeotropic point of normal-propyl alcohol and water is 87.7° C., which is a condition under which it is difficult to separate isopropyl alcohol, normal-propyl alcohol, and water from one another, and thus, it is difficult to accurately separate only normal-propyl alcohol from the normal-propyl alcohol purification tower 30 in the related art.

Further, since a small amount of normal-propyl alcohol is separated from the top of the azeotropic distillation purification tower 10 in the related art and then transferred to a subsequent purification process, a small amount of normal-propyl alcohol is present in the final product, and thus, it is impossible to produce ultrapure isopropyl alcohol.

Accordingly, the present application has been made in an effort to provide a purification method of isopropyl alcohol, which may produce ultrapure isopropyl alcohol by first removing water before removing normal-propyl alcohol.

The purification method of isopropyl alcohol according to an exemplary embodiment of the present application comprises: feeding a feed comprising: isopropyl alcohol, water, and a byproduct comprising normal-propyl alcohol to an azeotropic distillation purification tower; separating an azeotrope comprising isopropyl alcohol, normal-propyl alcohol, and water from the top of the azeotropic distillation purification tower and feeding the azeotrope to a dehydration tower; separating the isopropyl alcohol and the normal-propyl alcohol from the bottom of the dehydration tower and feeding the isopropyl alcohol and the normal-propyl alcohol to a normal-propyl alcohol purification tower; and separating the isopropyl alcohol from the top of the normal-propyl alcohol purification tower.

The purification method of isopropyl alcohol according to an exemplary embodiment of the present application comprises: feeding a feed comprising isopropyl alcohol, water, and a byproduct comprising normal-propyl alcohol to an azeotropic distillation purification tower.

In an exemplary embodiment of the present application, the feed comprising isopropyl alcohol, water, and a byproduct comprising normal-propyl alcohol may be a reactant produced from a reaction process of propylene and water. In this case, the byproduct comprising normal-propyl alcohol may further comprise one or more of ether, acetone, and the like in addition to normal-propyl alcohol.

The purification method of isopropyl alcohol according to an exemplary embodiment of the present application comprises: separating an azeotrope comprising isopropyl alcohol, normal-propyl alcohol, and water from the top of the azeotropic distillation purification tower and feeding the azeotrope to a dehydration tower.

In an exemplary embodiment of the present application, water may be separated from the bottom of the azeotropic distillation purification tower simultaneously with the separating of the azeotrope comprising isopropyl alcohol, normal-propyl alcohol, and water from the top of the azeotropic distillation purification tower.

The purification method of isopropyl alcohol according to an exemplary embodiment of the present application comprises: separating the isopropyl alcohol and the normal-propyl alcohol from the bottom of the dehydration tower and feeding the isopropyl alcohol and the normal-propyl alcohol to a normal-propyl alcohol purification tower.

In an exemplary embodiment of the present application, an azeotropic agent may be additionally fed to the dehydration tower. As the azeotropic agent, a material known in the art may be used, and more specifically, cyclohexane may be used, but the azeotropic agent is not limited thereto. Further, after the azeotropic agent is fed to the dehydration tower during the initial operation of the dehydration tower, the azeotropic agent is separated from the top of a water recovery tower, and then recycled to the dehydration tower, as will be described below.

In an exemplary embodiment of the present application, the purification method may further comprise: separating the azeotropic agent and the water from the top of the dehydration tower and feeding the azeotropic agent and the water to the water recovery tower. Further, in the water recovery tower, water may be separated from the bottom of the water recovery tower, the azeotropic agent may be separated from the top of the water recovery tower, and the separated azeotropic agent may be recycled to the dehydration tower.

The purification method of isopropyl alcohol according to an exemplary embodiment of the present application comprises: separating the isopropyl alcohol from the top of the normal-propyl alcohol purification tower.

In an exemplary embodiment of the present application, normal-propyl alcohol may be separated from the bottom of the normal-propyl alcohol purification tower, and the separated normal-propyl alcohol may be recycled to the above-described reaction process of propylene and water. Since the production reaction of isopropyl alcohol according to the reaction process of propylene and water is an equilibrium reaction with ether and normal-propyl alcohol, the selectivity of isopropyl alcohol may be more improved by recycling the normal-propyl alcohol separated from the normal-propyl alcohol purification tower to a reaction process of propylene and water.

According to an exemplary embodiment of the present application, it is possible to increase the separation efficiency of isopropyl alcohol (IPA) and normal-propyl alcohol (NPA) because water is removed by feeding the azeotrope comprising isopropyl alcohol, normal-propyl alcohol, and water to the dehydration tower, and then the isopropyl alcohol and the normal-propyl alcohol are separated in the normal-propyl alcohol purification tower. More specifically, since isopropyl alcohol and normal-propyl alcohol have a boiling point of 82.5° C. and 97.2° C., respectively, isopropyl alcohol and normal-propyl alcohol may be easily separated when there is no water. Accordingly, according to an exemplary embodiment of the present application, it is possible to increase the separation efficiency of isopropyl alcohol and normal-propyl alcohol in the normal-propyl alcohol purification tower by first removing water before the feed is fed to the normal-propyl alcohol purification tower.

In an exemplary embodiment of the present application, the number of theoretical plates of the normal-propyl alcohol purification tower may be 40 to 80, 45 to 75, and 50 to 70. When the number of theoretical plates of the normal-propyl alcohol purification tower is less than 40, the improvement in separation efficiency may be minimal, and when the number of theoretical plates of the normal-propyl alcohol purification tower is more than 80, investment costs for devices may be excessive, which is not preferred.

A process diagram of a purification method of isopropyl alcohol according to an exemplary embodiment of the present application is schematically illustrated in FIG. 2.

As illustrated in FIG. 2, the purification method of isopropyl alcohol according to an exemplary embodiment of the present application comprises: feeding a feed 50 comprising: isopropyl alcohol, water, and a byproduct comprising normal propyl alcohol to an azeotropic distillation purification tower 10; separating an azeotrope comprising isopropyl alcohol, normal-propyl alcohol, and water from the top of the azeotropic distillation purification tower 10 and feeding the azeotrope to a dehydration tower 20; separating the isopropyl alcohol and the normal-propyl alcohol from the bottom of the dehydration tower 20 and feeding the isopropyl alcohol and the normal-propyl alcohol to a normal-propyl alcohol purification tower 30; and separating the isopropyl alcohol from the top of the normal propyl alcohol purification tower 30. Further, the purification method may further comprise: separating an azeotropic agent and water from the top of the dehydration tower 20 and feeding the azeotropic agent and the water to a water recovery tower 40, and may further comprise: separating the azeotropic agent from the top of the water recovery tower 40 and recycling the azeotropic agent to the dehydration tower 20.

In an exemplary embodiment of the present application, the azeotropic distillation purification tower, the dehydration tower, the normal-propyl alcohol purification tower, the water recovery tower, and the like are a distillation device comprising a reboiler, a condenser, a column, and the like, and may adopt a distillation device known in the art, and is not particularly limited.

In an exemplary embodiment of the present application, the content of isopropyl alcohol may be 99.8 wt % or more, 99.9 wt % or more, and less than 100 wt %, based on the total weight of a purified product by the purification method of isopropyl alcohol. When the content of isopropyl alcohol is less than 99.8 wt % based on the total weight of the purified product, ultrapure isopropyl alcohol cannot be prepared due to byproducts other than the isopropyl alcohol, and accordingly, many constraints may occur when isopropyl alcohol is used in various uses comprising the use as a cleaning agent in the electronic industry such as the manufacture of semiconductors and liquid crystal display (LCD).

Hereinafter, the present application will be described in detail with reference to Examples for specifically describing the present application. However, the Examples according to the present application may be modified in various forms, and it is not interpreted that the scope of the present application is limited to the Examples described in detail below. The Examples of the present application are provided for more completely explaining the present application to the person with ordinary skill in the art.

EXAMPLES

Examples 1 to 3 and Comparative Examples 1 to 4

In the Examples, isopropyl alcohol was purified according to the process diagram illustrated in FIG. 2, and in the Comparative Examples, the process of purifying isopropyl alcohol was performed according to the process diagram illustrated in FIG. 1. The number of theoretical plates of each process and the fed energy in the Examples and the Comparative Examples are shown in the following Table 1.

TABLE 1

|  | Azeotropic distillation purification tower | | Dehydration tower | | NPA purification tower | | Water recovery tower | | |
| --- | --- | --- | --- | --- | --- | --- | --- | --- | --- |
|  | Number of theoretical plates | Q | Number of theoretical plates | Q | Number of theoretical plates | Q | Number of theoretical plates | Q | Total Q (Gcal/hr) |
| Example 1 | 55 | 3.17 | 36 | 2.64 | 50 | 1.66 | 34 | 0.23 | 7.70 |
| Example 2 | 55 | 3.17 | 36 | 2.64 | 60 | 1.66 | 34 | 0.23 | 7.70 |
| Example 3 | 55 | 3.17 | 36 | 2.64 | 70 | 1.66 | 34 | 0.23 | 7.70 |
| Comparative Example 1 | 55 | 3.17 | 36 | 2.51 | 30 | 0.47 | 34 | 0.20 | 6.35 |
| Comparative Example 2 | 55 | 3.17 | 36 | 2.51 | 70 | 0.47 | 34 | 0.20 | 6.35 |
| Comparative Example 3 | 55 | 3.17 | 36 | 2.51 | 30 | 1.82 | 34 | 0.20 | 7.70 |
| Comparative Example 4 | 55 | 3.17 | 36 | 2.51 | 70 | 1.82 | 34 | 0.20 | 7.70 |

In Table 1, Q means an amount of energy fed to each process, and the unit thereof is Gcal/hr.

Experimental Example

The components of isopropyl alcohol purified according to Examples 1 to 3 and Comparative Examples 1 to 4 were analyzed, and the results are shown in the following Table 2. The component analysis of the purified isopropyl alcohol is a result obtained by a simulation with Aspen plus which is a chemical process simulator.

TABLE 2

|  | IPA (%) | NPA (ppm) | Water (ppm) |
| --- | --- | --- | --- |
| Example 1 | 99.97 | 54 | 202 |
| Example 2 | 99.98 | 16 | 202 |
| Example 3 | 99.98 | 5 | 202 |

TABLE 2-continued

|  | IPA (%) | NPA (ppm) | Water (ppm) |
| --- | --- | --- | --- |
| Comparative Example 1 | 99.93 | 506 | 202 |
| Comparative Example 2 | 99.93 | 506 | 202 |
| Comparative Example 3 | 99.97 | 78 | 202 |
| Comparative Example 4 | 99.97 | 78 | 202 |

As in the results in Comparative Example 2, when the number of plates of the NPA purification tower was increased in the process in the related art, there was no change in content of NPA in a final product, and as in the results in Comparative Example 3, when the energy fed to the NPA purification tower was increased in the process in the related art, the content of NPA in a final product was decreased. In addition, as in the result of Comparative Example 4, it could be confirmed that in the process in the related art, effects of an increase in energy to be fed were greater than effects of an increase in the number of plates of the NPA purification tower.

According to an exemplary embodiment of the present application, the flow rate of feed fed to the dehydration tower was increased by about 12% as compared to that of the process in the related art, so that the energy to be fed to the dehydration tower and the water recovery tower was increased.

As in the results, the purification method of isopropyl alcohol according to an exemplary embodiment of the present application may increase the separation efficiency of isopropyl alcohol (IPA) and normal-propyl alcohol (NPA) because water is removed by feeding the azeotrope comprising isopropyl alcohol, normal-propyl alcohol, and water to the dehydration tower, and then the isopropyl alcohol and the normal-propyl alcohol are separated.

Further, since the purification method of isopropyl alcohol according to an exemplary embodiment of the present application may minimize the content of normal-propyl alcohol in a final product, ultrapure (99.8 wt % or more) isopropyl alcohol may be prepared.

The invention claimed is:

1. A method for purifying isopropyl alcohol, the method comprising:
   feeding a feed comprising: isopropyl alcohol, water, and a byproduct comprising normal propyl alcohol to an azeotropic distillation purification tower;

separating and discharging an azeotrope comprising isopropyl alcohol, normal-propyl alcohol, and water from a top of the azeotropic distillation purification tower and feeding the azeotrope to a dehydration tower;

separating and discharging isopropyl alcohol and normal-propyl alcohol as a first bottom stream from a bottom of the dehydration tower and feeding the first bottom stream to a normal-propyl alcohol purification tower;

separating and discharging isopropyl alcohol as a first top stream from a top of the normal-propyl alcohol purification tower; and separating and discharging normal-propyl alcohol from a bottom of the normal-propyl alcohol purification tower and recycling the normal-propyl alcohol to the a reaction of propylene and water, wherein the feed comprising isopropyl alcohol, water, and a byproduct comprising normal-propyl alcohol is a product of the reaction of propylene and water.

2. The method of claim 1, wherein water is discharged as a second bottom stream from a bottom of the azeotropic distillation purification tower.

3. The method of claim 1, wherein an azeotropic agent is additionally fed to the dehydration tower.

4. The method of claim 3, further comprising:
separating and discharging the azeotropic agent and water as a second top stream from a top of the dehydration tower and feeding the second top stream to a water recovery tower.

5. The method of claim 4, further comprising:
separating and discharging the azeotropic agent from a top of the water recovery tower and recycling the azeotropic agent to the dehydration tower.

6. The method of claim 4, further comprising:
separating and discharging water from a bottom of the water recovery tower.

7. The method of claim 1, wherein a number of theoretical plates of the normal-propyl alcohol purification tower is from 40 to 80.

8. The method of claim 1, wherein a content of the isopropyl alcohol in the first bottom stream is 99.8 wt % or more based on a total weight of a the first bottom stream.

* * * * *